US011591632B2

(12) United States Patent
Lee et al.

(10) Patent No.: US 11,591,632 B2
(45) Date of Patent: Feb. 28, 2023

(54) GENETICALLY-MUTATED BACTERIAL STRAIN FOR DETECTING ESTROGENIC COMPOUND AND METHOD FOR DETECTING ESTROGENIC COMPOUND USING THE SAME

(71) Applicant: INDUSTRY-UNIVERSITY COOPERATION FOUNDATION HANYANG UNIVERSITY, Seoul (KR)

(72) Inventors: Jin-Won Lee, Seoul (KR); Myung Chan Gye, Gyeonggi-do (KR); Su-Hyun Ryu, Gyeonggi-do (KR); Young-Pil Kim, Seoul (KR)

(73) Assignee: INDUSTRY-UNIVERSITY COOPERATION FOUNDATION HANYANG UNIVERSITY, Seoul (KR)

( * ) Notice: Subject to any disclaimer, the term of this patent is extended or adjusted under 35 U.S.C. 154(b) by 1172 days.

(21) Appl. No.: 16/146,677

(22) Filed: Sep. 28, 2018

(65) Prior Publication Data
US 2019/0127774 A1 May 2, 2019

Related U.S. Application Data

(63) Continuation of application No. PCT/KR2017/001713, filed on Feb. 16, 2017.

(30) Foreign Application Priority Data

Mar. 30, 2016 (KR) ........................ 10-2016-0038444

(51) Int. Cl.
| | | |
|---|---|---|
| C12N 15/74 | (2006.01) | |
| C12Q 1/02 | (2006.01) | |
| C07K 14/47 | (2006.01) | |
| C12N 15/70 | (2006.01) | |
| C07K 14/72 | (2006.01) | |
| C07K 14/245 | (2006.01) | |
| C07K 14/195 | (2006.01) | |
| G01N 33/52 | (2006.01) | |

(52) U.S. Cl.
CPC ............ C12Q 1/025 (2013.01); C07K 14/195 (2013.01); C07K 14/245 (2013.01); C07K 14/4702 (2013.01); C07K 14/72 (2013.01); C07K 14/721 (2013.01); C12N 15/70 (2013.01); C12N 15/74 (2013.01); C12Q 1/02 (2013.01); G01N 33/52 (2013.01); C07K 2319/43 (2013.01)

(58) Field of Classification Search
None
See application file for complete search history.

(56) References Cited

U.S. PATENT DOCUMENTS 6,200,759 B1   3/2001   Dove et al.

FOREIGN PATENT DOCUMENTS

| KR | 10-2004-0028321 | 4/2004 |
| KR | 10-2004-0039082 | 5/2004 |
| KR | 10-0476342 | 5/2004 |

OTHER PUBLICATIONS

Adler, Marlen, "Bacterial Two-hybrid Screening to Study the Role of Crescentin Generating Cell Curvature of *Caulobacter crescentus*" Degree project in biology, Bachelor of Science, 2008, Uppsala University, 18 pages.
Campana, et al., "Cell-based assays for screening androgen receptor ligands", Semin Reprod Med. 2015, May 33(3): 225-234.
Collins et al., "The estrogenic and antiestrogenic activities of phytochemicals with the human estrogen receptor expressed in yeast", Steroids 62:365-372, 1997.
Nishihara et al., "Estrogenic Activities of 517 Chemicals by Yeast Two-Hybrid Assay", Journal of Health Science, 46(4) 282-298 (2000).
Chen et al., Acute Toxicity, Mutagenicity, and Estrogenicity of Bisphenol-A and Other Bisphenols, Environ Toxicol., Feb. 2002; 17(1):80-86.
Suzuki et al., "Removal of estrogenic activities of 17β-estradiol and ethinylestradiol by ligninolytic enzymes from white rot fungi", Water Research 37 (2003), pp. 1972-1975.
Lee et al., "Construction of the Detection System of Endocrine Disrupters using Yeast Two-Hybrid System with Human Estrogen Receptor Ligand Binding Domain and Co-activators", Environmental Mutagens & Carcinogens 22-3: 175-182 (2002), English Abstract Only Consid.

(Continued)

*Primary Examiner* — Jennifer E Graser
(74) *Attorney, Agent, or Firm* — Sughrue Mion, PLLC

(57) ABSTRACT

The present invention relates to a genetically mutated bacteria strain for detecting an estrogenic compound and a method for detecting an estrogenic compound by using the same. More specifically, the present invention relates to a bacteria strain having an ability to detect an estrogenic compound, transformed by plasmid A comprising base sequences in which a gene for encoding a coactivator interacting with an estrogen receptor ligand binding domain (ER LBD) is conjugated to a gene for encoding λCI protein, and plasmid B in which a gene for encoding an estrogen receptor ligand binding domain (ER LBD) is conjugated to a gene for encoding αNTD protein, and a method for detecting an estrogenic compound by using same.
The present invention can provide genetically mutated bacteria for detecting an estrogenic compound and a method for detecting an estrogenic compound by using same since the bacteria are based on estrogen receptor protein originated from the human body, and thus are environmentally friendly, and the detection of the bacteria can be performed in a very short time with low cost and labor by virtue of a relatively simple process.

10 Claims, 6 Drawing Sheets

Specification includes a Sequence Listing.

(56) References Cited

OTHER PUBLICATIONS

Lee et al., "Employment of the Human Estrogen Receptor β Ligand-Binding Domain and Co-Activator SRC1 Nuclear Receptor-Binding Domain for the Construction of a Yeast Two-Hybrid Detection System for Endocrine Disrupters", J. Biochem., v. 131, p. 399-405 (2002).

McRobb et al., "In Silico Identification and Pharmacological Evaluation of Novel Endocrine Disrupting Chemicals That Act via the Ligand-Binding Domain of the Estrogen Receptor α", Toxicological Sciences, 141(1), 2014, 188-197 (2014).

[FIG. 1]
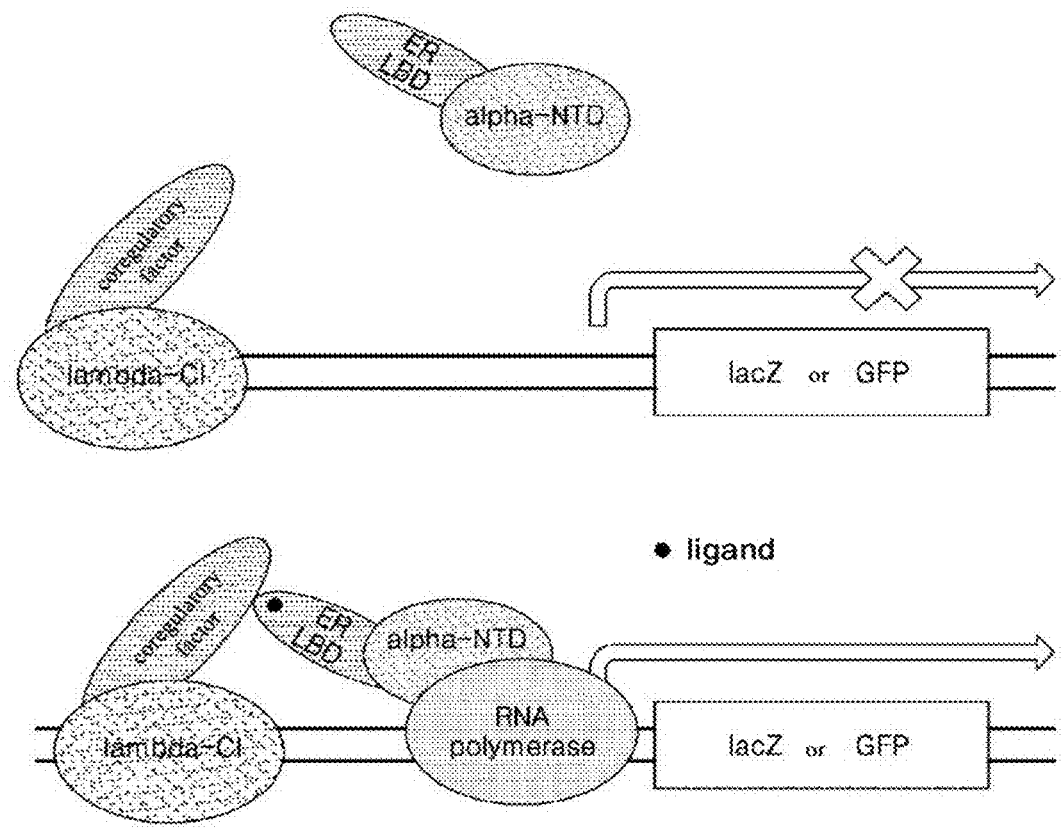
[FIG. 2A]
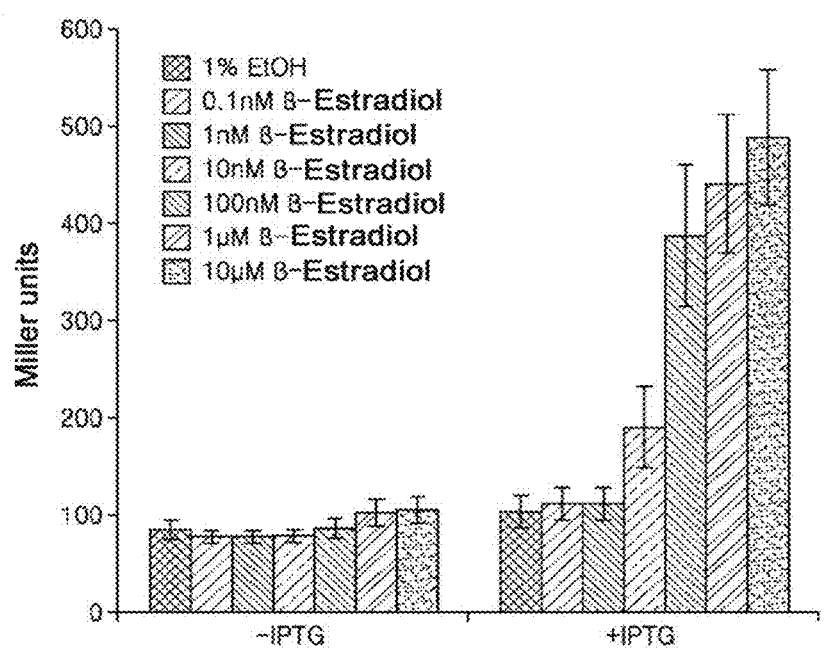

[FIG. 2B]
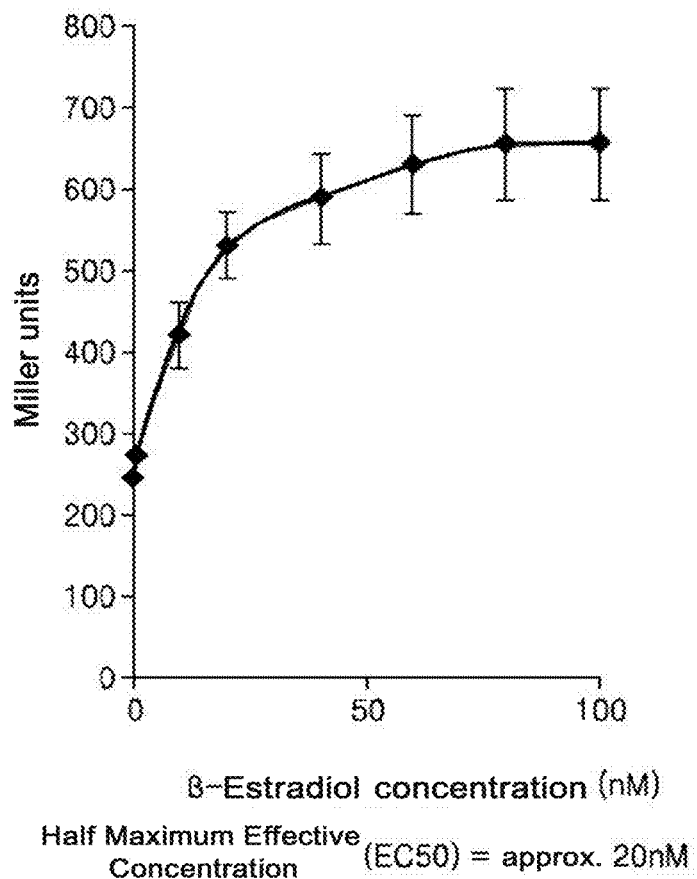
[FIG. 3]
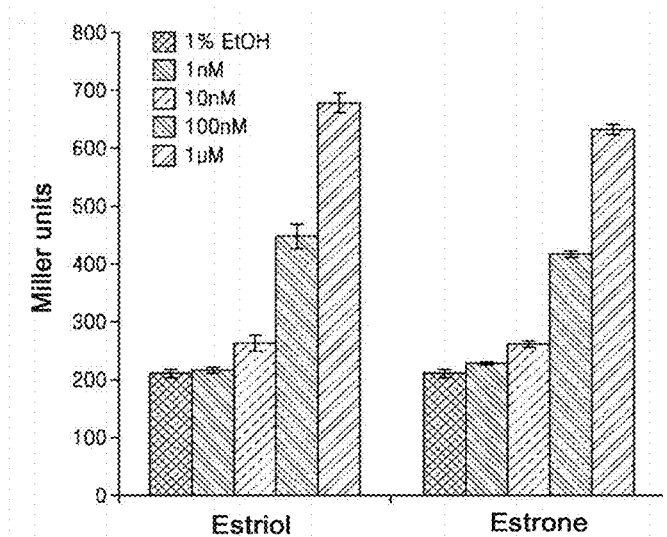

[FIG. 4A]
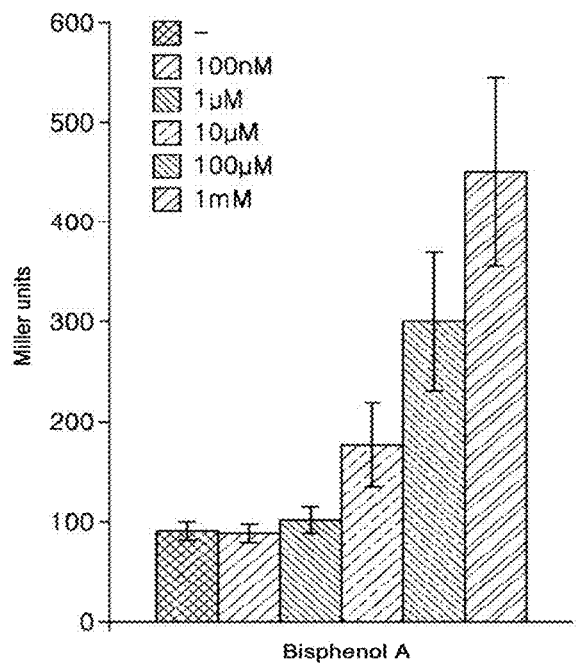
[FIG. 4B]
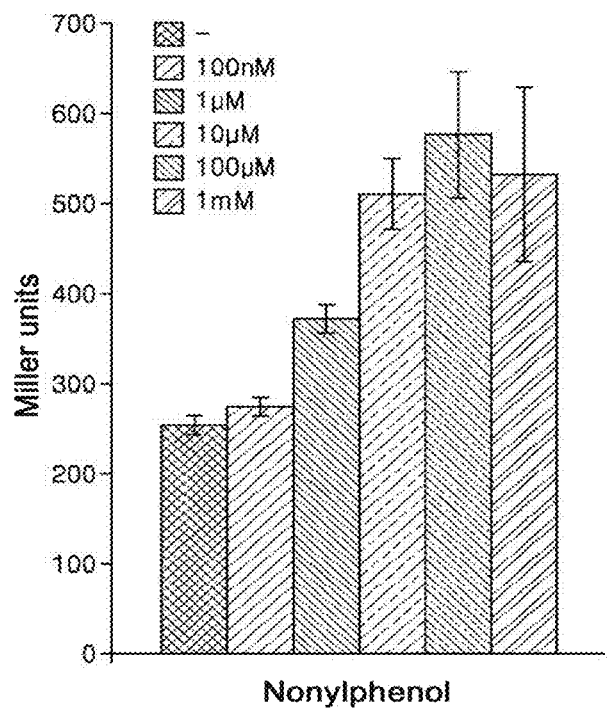

[FIG. 5]
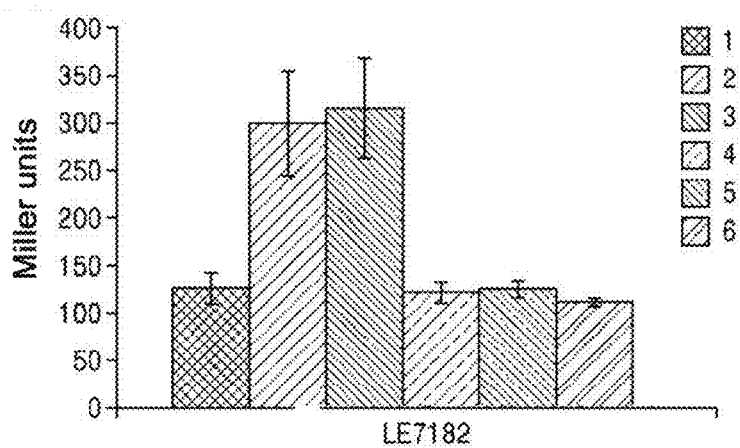
1 : control group
2 : receipt paper (0.5cm × 0.5cm direct contact)
3 : receipt paper (Bisphenol A-free) (0.5cm × 0.5cm direct contact)
4 : disposable cup (0.5cm × 0.5cm direct contact)
5 : hot water + disposable cup (0.5cm × 0.5cm direct contact)
6 : shampoo
[FIG. 6]
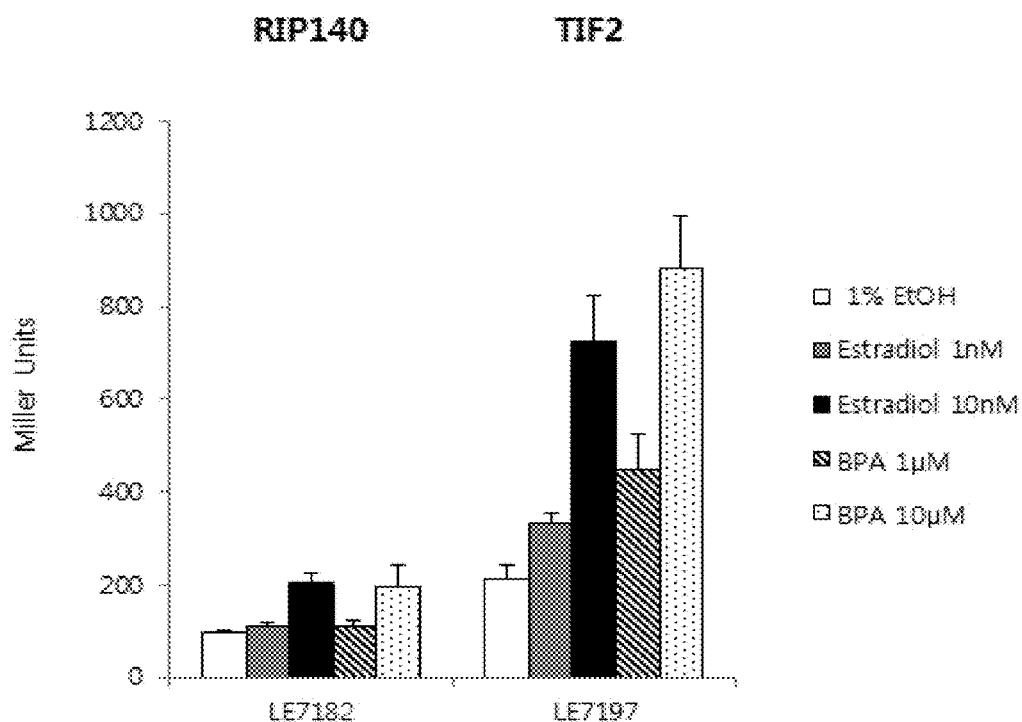

[FIG. 7]
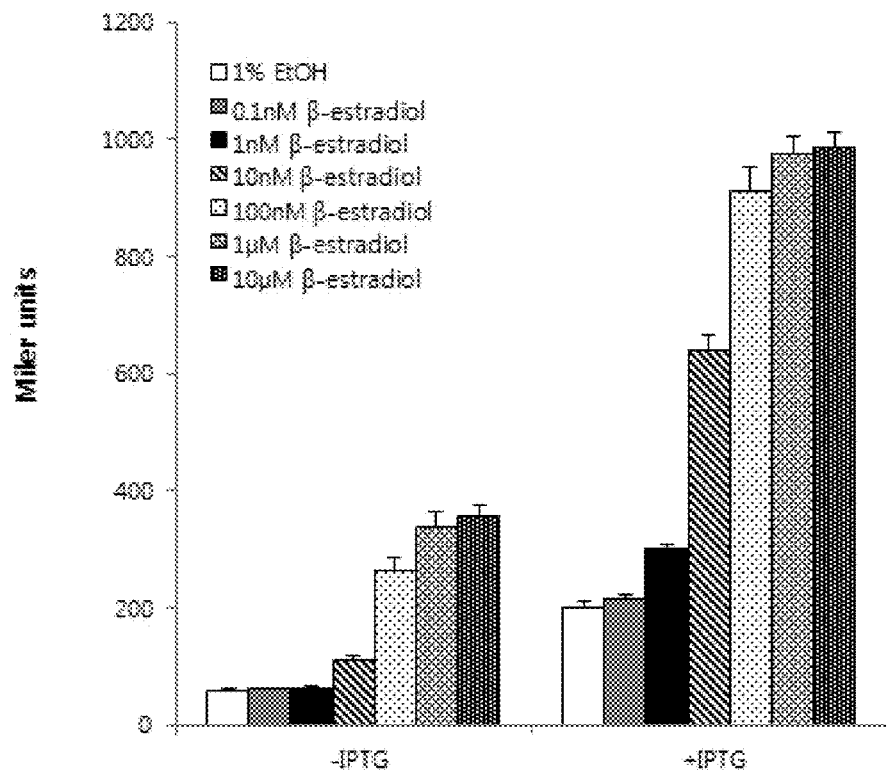
[FIG. 8]
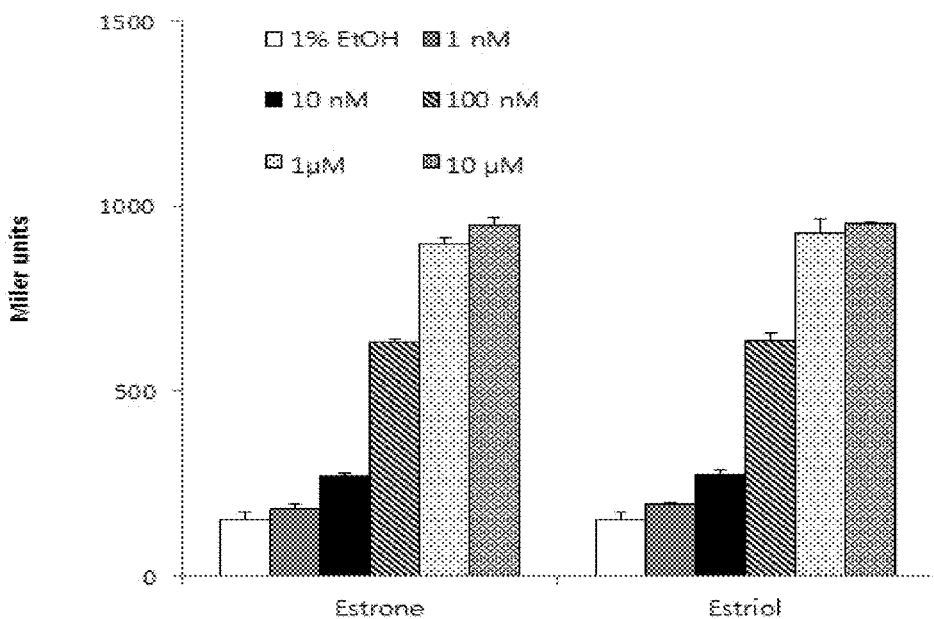

[FIG. 9]
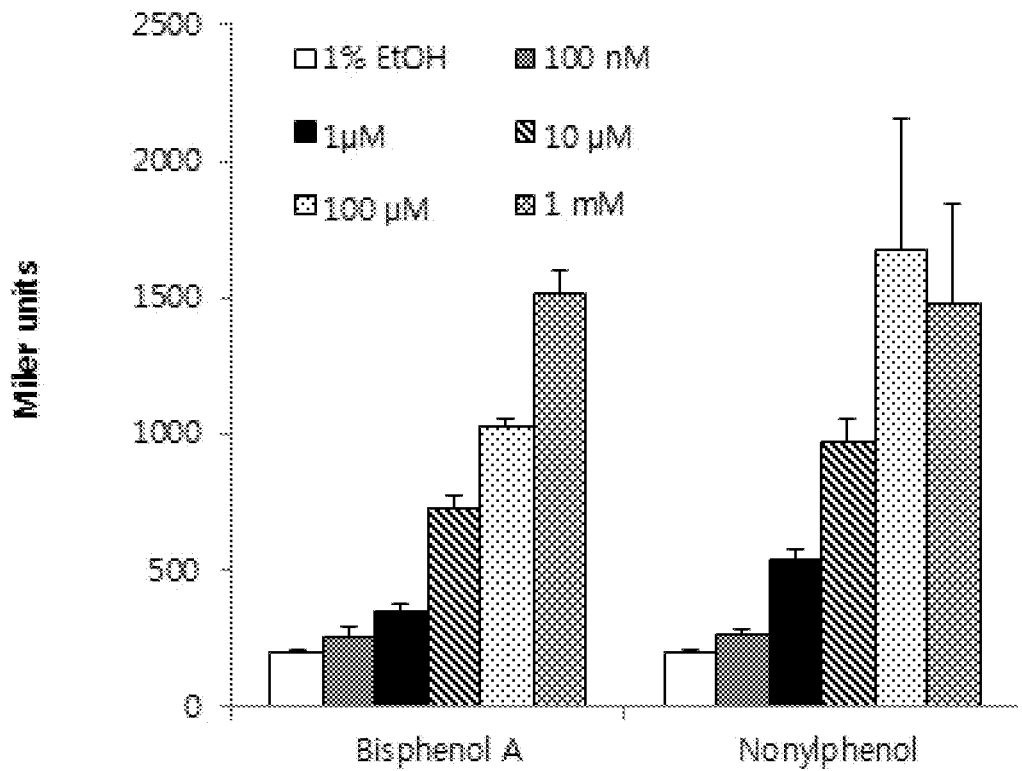
[FIG. 10]
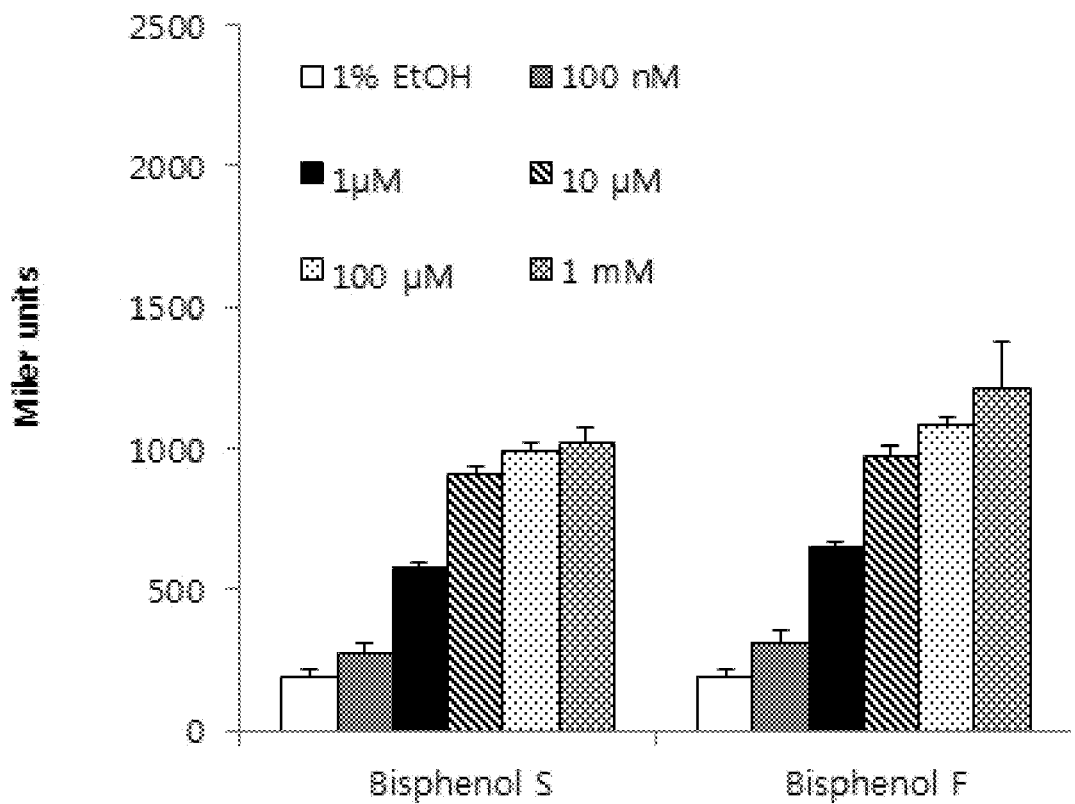

GENETICALLY-MUTATED BACTERIAL STRAIN FOR DETECTING ESTROGENIC COMPOUND AND METHOD FOR DETECTING ESTROGENIC COMPOUND USING THE SAME

RELATED APPLICATION

This is a Continuation of the PCT international Application No. PCT/KR2017/001713 filed Feb. 16, 2017, which claims benefit of priority of Korean Patent Application No. 10-2016-0038444 filed Mar. 30, 2016. All applications identified in this section are incorporated herein by reference; each in its entirety.

SEQUENCE STATEMENT

Incorporated by reference herein in its entirety is the Sequence Listing entitled "P018-027-US_sequence_list," created Nov. 20, 2018, size of 23 kilobytes.

SEQUENCE STATEMENT

Incorporated by reference herein in its entirety is the Sequence Listing entitled "P018-027-US_sequence_list," created Jan. 6, 2019, size of 21 kilobytes.

SEQUENCE STATEMENT

Incorporated by reference herein in its entirety is the Sequence Listing entitled "PCTKR2017001713-seql-," created Feb. 16, 2017, size of 17 KB.

TECHNICAL FIELD

The present invention relates to a genetically-modified bacterial strain for detecting an estrogenic compound and a method for detecting an estrogenic compound using the same.

BACKGROUND ART

Endocrine disrupting compounds (EDCs) refer to a group of compounds exhibiting adverse effects on humans and wildlife due to mimicry, blocking or disruption of the physiological action of a hormone. The American Endocrinology Society has reported the finding that endocrine disruptors may affect male and female reproduction, breast development, cancer, prostate cancer, the neuroendocrine system, thyroid activity, metabolism, obesity and the cardiovascular endocrine system, and warned that EDCs can raise serious concerns about public health.

Hormones serve to cause a variety of responses and normal biological functions such as growth, development, behaviors and reproduction by interacting with receptors of target cells. However, substances causing interference with the activity of hormones such as the EDCs described above may result in a variety of reversible and non-reversible biological impairments including dwarf growth, short-term memory impairment, tubal pregnancy, low sperm number, reproductive disorders, and the impairment of the immune system.

Generally, EDCs may be classified into three major groups, including androgenic EDCs (compounds that mimic or block natural testosterone), thyroid-related EDCs (compounds that directly or indirectly affect the thyroid) and estrogenic EDCs (compounds that mimic or block natural estrogen). Particularly, among these, estrogenic compounds (ECs) are known to be closely related to sex development and disorders of children, as well as adult males and females, and the occurrence of cancer, and have very high severity because they are found in thousands of products that are commonly used in daily life.

It has been widely reported that EDCs containing estrogen are present in a very low concentration in the environment, but due to relatively high fat solubility, they are accumulated in the fat of creatures and animals in high positions in the food chain, resulting in considerable physiological responses even at relatively low concentrations. In addition, they are also found in industrial chemicals such as pesticides, herbicides, fungicides, plasticizers, plastics, resins and detergents.

To date, as methods of detecting estrogens and estrogen-like compounds in a sample, analytical methods such as solid phase extraction (SPE), high performance liquid chromatography (HPLC), liquid chromatography/mass spectrometry (LC/MS) and gas chromatography/mass spectrometry (GC/MS) are known. These methods require not only a high equipment cost, but also a high production cost and a lot of time because of a complicated analytic process.

Regarding the detection methods, a yeast two-hybrid system, which is a molecular biology technique used to detect protein-protein interactions or protein-DNA interactions, is based upon the activation of a downstream reporter gene by the binding of a transcription factor to an upstream activating sequence (UAS). In this case, the transcription factor is split into two fragments, called a binding domain (BD) and an activating domain (AD), and the BD is the domain responsible for binding to the UAS and the AD is the domain responsible for the activation of transcription.

Conventionally, while techniques of analyzing the estrogenic activity of estrogenic compounds using such yeast-protein hybridization have been reported (Non-Patent Literature 1: Journal of Health Science Vol. 46 (2000), No. 4, pages 282-298; Non-Patent Literature 2: Steroids, Vol. 62, Issue 4, April 1997, pages 365-372.), yeasts involved in sensing estrogens and environmental hormones need a lot of time and effort to grow a strain, a considerable amount of time for sensing, and very low stability.

Thus, techniques for bacterial protein hybridization using bacteria instead of yeasts, which are eukaryotic microorganisms, have been reported, and they are methods for confirming materials capable of regulating protein-protein interactions using genetically-modified prokaryotic cells containing a reporter gene, a first chimeric gene, a second chimeric gene and the like as components (Patent Literature 1, U.S. Pat. No. 6,200,759).

However, techniques which are optimized to analyze a variety of estrogenic substances capable of affecting humans, facilitate detection of various substances which are impossible to be detected by a conventional molecule-based sensor and can solve problems of instability of a yeast-based sensor and long detection time have not been reported to date.

DISCLOSURE

Technical Problem

Therefore, to solve the problems of the conventional art, the present invention provides a genetically-modified bacterial strain for detecting an estrogenic compound, which is environmentally-friendly since it is based on an estrogen receptor protein derived from the human body, and takes a very short detection time with a low cost and a low amount of labor due to a relatively simple process, and a method for detecting an estrogenic compound using the same.

Technical Solution

To solve the above-mentioned problems, the present invention provides a bacterial strain having an ability of detecting an estrogenic compound, the strain being transformed by plasmid A having a base sequence in which a gene encoding a coregulatory factor interacting with an estrogen receptor ligand-binding domain (ER LBD) is conjugated with a gene encoding a λCI protein, and plasmid B in which a gene encoding ER LBD is conjugated with a gene encoding an αNTD protein.

According to an exemplary embodiment of the present invention, the coregulatory factor interacting with the ER LBD may be any one selected from the group comprising a RIP140 protein, a TIF2 protein, a TIF1 protein and a SRC1 protein.

According to another exemplary embodiment of the present invention, the gene encoding the coregulatory factor interacting with the ER LBD or the gene encoding the ER LBD may be obtained by transcribing mRNA from human genomic DNA, preparing intron-deleted mRNA through splicing with respect to the mRNA, and amplifying the intron-deleted mRNA by PCR using cDNA synthesized by reverse transcription as a template.

According to still another exemplary embodiment of the present invention, a FLAG sequence for confirming the expression of the RIP40 protein and the λCI protein may be conjugated to the 3'-end of the gene encoding the RIP40 protein.

According to yet another exemplary embodiment of the present invention, a FLAG sequence for confirming the expression of the TIF2 protein and the λCI protein may be conjugated to the end of the gene encoding the TIF2 protein.

According to yet another exemplary embodiment of the present invention, the plasma A may have a nucleic acid sequence of SEQ ID NO: 1 or 3.

According to yet another exemplary embodiment of the present invention, a FLAG sequence for confirming the expression of the ER LBD and the αNTD protein may be conjugated to the 3'-end of the gene encoding the ER LBD.

According to yet another exemplary embodiment of the present invention, the plasmid B may have a nucleic acid sequence of SEQ ID NO: 2.

According to yet another exemplary embodiment of the present invention, the bacterial strain may be any one strain selected from the group comprising *Escherichia coli* (*E. coli*), *Bacillus subtilis*, *Bacillus licheniformis* and lactic acid bacteria.

According to yet another exemplary embodiment of the present invention, the estrogenic compound may be selected from the group comprising norethynodrel, 5α-androstane, nonylphenol, dodecylphenol, octylphenol, bisphenol A, bisphenol S, bisphenol F, 2-ethylhexyl-4-hydroxybenzoate, 4,4'-dihydroxybenzophenone, 2,4-dihydroxybenzophenone, dihydroxymethoxychlorolefin, o,p'-DDT, dihydroxymethoxychlor (HP 1E), 2',3',4',5'-tetrachloro-4-biphenylol, nordihydroguaiaretic acid, aurin, phenolphthalein, phenol red, and a mixture thereof.

To solve another problem described above, the present invention provides a method for detecting an estrogenic compound, which includes:

preparing the bacterial strain having an ability of detecting an estrogenic compound described above;

culturing the bacterial strain to which a specimen containing an estrogenic compound is added; and lysing the cultured bacterial strain and analyzing a degree of the expression of a reporter protein.

According to an exemplary embodiment of the present invention, the reporter protein may be a β-galactosidase, a fluorescent protein or an antibiotic resistance-imparting protein.

According to another exemplary embodiment of the present invention, the fluorescent protein may be a green fluorescent protein (GFP), a yellow fluorescent protein (YFP), a red fluorescent protein (RFP) or a luciferase.

According to still another exemplary embodiment of the present invention, the degree of the expression of a reporter protein may be measured using a UV-VIS spectrophotometer.

According to yet another exemplary embodiment of the present invention, a degree of the expression of the β-galactosidase may be measured by adding O-nitrophenyl-β-D-galactopyranoside (ONPG) as a colorimetric reagent after the lysis, and analyzing an expression degree.

Advantageous Effects

According to the present invention, a genetically-modified bacterial strain for detecting an estrogenic compound, which is environmentally-friendly since it is based on an estrogen receptor protein derived from the human body, and takes a very short detection time with a low cost and a low amount of labor due to a relatively simple process, and a method for detecting an estrogenic compound using the same can be provided.

DESCRIPTION OF DRAWINGS

FIG. 1 is a schematic diagram illustrating the case in which a reporter gene is not expressed in the absence of an estrogenic compound (top) and the case in which a reporter gene is expressed by binding of an estrogenic compound to ER LBD (bottom) in bacteria according to the present invention.

FIG. 2A is a graph illustrating the result of confirming an ability of a strain according to the present invention to detect a representative estrogenic compound such as 17β-estradiol.

FIG. 2B is a graph illustrating the result of confirming an ability of a strain according to the present invention to detect a representative estrogenic compound such as 17β-estradiol.

FIG. 3 is a graph illustrating the result of confirming an ability of a strain according to the present invention to detect estrogenic compounds such as estriol and estrone.

FIG. 4A is a graph illustrating the result of confirming an ability of a strain according to the present invention to detect representative environmental hormones such as bisphenol A and nonylphenol.

FIG. 4B is a graph illustrating the result of confirming an ability of a strain according to the present invention to detect representative environmental hormones such as bisphenol A and nonylphenol.

FIG. 5 is a graph illustrating the result of confirming an ability of a strain according to the present invention to detect environmental hormones present in various articles which are available in daily life.

FIG. 6 is a graph illustrating the result of an experiment for comparing the sensitivities of sensor strains using a TIF2 protein and a RIP140 protein, as coregulatory factors interacting with ER LBD according to the present invention, respectively, with respect to a representative estrogen such as estradiol and a representative environmental hormone substance such as bisphenol A.

FIG. 7 is a graph illustrating the result of an experiment for confirming the sensitivity of a sensor strain using a TIF2 protein as a coregulatory factor interacting with ER LBD according to the present invention with respect to various concentrations of estradiol.

FIG. 8 is a graph illustrating an experiment for confirming the sensitivity of a sensor strain using a TIF2 protein as a coregulatory factor interacting with ER LBD according to the present invention with respect to various concentrations of estrone and estriol.

FIG. 9 is a graph illustrating the result of an experiment for confirming the sensibility of a sensor strain using a TIF2 protein as a coregulatory factor interacting with ER LBD according to the present invention with respect to various concentrations of bisphenol A and nonylphenol.

FIG. 10 is a graph illustrating the result of an experiment for confirming the sensibility of a sensor strain using a TIF2 protein as a coregulatory factor interacting with ER LBD according to the present invention with respect to various concentrations of bisphenol S and bisphenol F.

MODES OF THE INVENTION

Hereinafter, the present invention will be described in further detail. In the present invention, to detect an estrogen hormone and various estrogenic compounds, the principle of expressing a reporter gene by specific binding between a coregulatory factor interacting with ER LBD and an ER LBD protein was utilized. That is, when estrogenic compounds are present in a specimen subject to analysis, a corresponding estrogenic compound binds to the ER LBD, thereby forming the interaction between two proteins, and because of the interaction, the expression of a reporter gene is achieved. In addition, the expressed reporter gene is subjected to a color reaction by a colorimetric reagent, and by quantifying a degree of the color reaction, the concentration of the estrogenic compound in the specimen can be exactly quantified.

Therefore, the present invention provides genetically-modified bacteria for detecting an estrogenic compound, and the bacteria according to the present invention have an ability of detecting an estrogenic compound and are transformed by plasmid A having a base sequence in which a gene encoding a coregulatory factor interacting with ER LBD is conjugated with a gene encoding a λCI protein, and plasmid B in which a gene encoding ER LBD is conjugated with a gene encoding an αNTD protein.

As described above, conventionally, a yeast-based yeast two-hybrid system has been used to detect protein-protein interactions or protein-DNA interactions, but compared to bacteria, yeast has a very high similarity to humans in terms of a gene sequence. For example, yeast contains a protein similar to a coactivator such as human DP97 or REA. Therefore, such proteins are likely to interfere with sensing of an environmental hormone by binding to an estrogen receptor while the environmental hormone is actually sensed by the yeast two-hybrid system. Furthermore, since there are many possibilities for yeast to have proteins, other than the above-described DP97 or REA, capable of binding to an estrogen receptor, the bacteria-based detection method according to the present invention is more advantageous than the yeast two-hybrid system.

When the estrogen receptor protein binds to ligand compounds such as an estrogen, it may bind with a coregulatory factor protein which assists or suppresses a protein activity. In other words, in the present invention, as the ER LBD binding to an estrogenic compound as a ligand is coupled with a coregulatory protein, the estrogenic compound may be detected by a phenomenon of the expression of a reporter gene.

FIG. 1 is a schematic diagram illustrating the case in which a reporter gene is not expressed in the absence of an estrogenic compound (top) and the case in which a reporter gene is expressed by binding of an estrogenic compound to ER LBD (bottom) in bacteria according to the present invention (examples of the reporter gene include lacZ and GFP genes).

The bacteria according to the present invention are bacteria transformed by two types of plasmids, each type of plasmid encoding a protein set involved in the expression of a reporter gene. First, the plasmid A contains a gene encoding a coregulatory factor interacting with ER LBD (represented as a "coactivator" in FIG. 1) and a gene encoding a λCI protein, and the plasmid B contains genes encoding ER LBD and an αNTD protein.

Referring to FIG. 1, the bacteria according to the present invention regulate the expression of a reporter gene by protein sets produced by the two types of plasmids. That is, the coregulatory factor protein and the λCI protein which are expressed by the plasmid A bind upstream of a reporter gene, and the ER LBD and the αNTD protein which are expressed by the plasmid B bind to an RNA polymerase. At this time, to express the reporter gene, it is necessary to have an interaction between a set of the coregulatory factor protein and the λCI protein and a set of the ER LBD and the αNTD protein. Referring to the top view of FIG. 1, when there is no estrogenic compound acting as a ligand, there is no interaction between a set of the coregulatory factor protein and the λCI protein and a set of ER LBD and the αNTD protein, and therefore, the reporter gene is not expressed. Meanwhile, referring to the bottom view of the FIG. 1, when there is an estrogenic compound as a ligand, the estrogenic compound binds to ER LBD, thereby the interaction between a set of the coregulatory factor protein and the λCI protein and a set of ER LBD and the αNTD protein is formed, resulting in the expression of the reporter gene. Therefore, with the bacteria according to the present invention, only when an estrogenic compound is present in a specimen subjected to analysis, a protein may be produced by the expression of the reporter gene.

According to the present invention, as the coregulatory factor protein, any one of various types of coregulatory factors or coactivator proteins, which can interact with ER LBD, may be used, but the present invention is not limited thereto. For example, as the coregulatory factor protein, any one of the proteins selected from the group comprising a RIP140 protein, a TIF2 protein, a TIF1 protein and a SRC1 protein may be considered.

The gene encoding the coregulatory factor interacting with ER LBD or the gene encoding ER LBD, which is included in the plasmid A or B, may be obtained by transcribing mRNA from human genomic DNA, preparing intron-deleted mRNA through splicing of the mRNA, and amplifying the intron-deleted mRNA by PCR using cDNA synthesized by reverse transcription with respect to the mRNA as a template.

In addition, a FLAG sequence for confirming expression of the coregulatory factor protein and the λCI protein may be additionally conjugated to the 3'-end of the gene encoding a coregulatory factor interacting with ER LBD, and in the same manner as described above, a FLAG sequence for confirming expression of the ER LBD and the αNTD protein may be additionally conjugated to the 3'-end of the gene encoding ER LBD. Because of the conjugation of such a FLAG sequence, only expressed proteins can be identified by western blotting recognizing such proteins as specific antibodies.

Specifically, when an RIP140 protein is used as a coregulatory factor, the plasmid A may have a nucleic acid sequence of SEQ ID NO: 1, and the plasmid B may have a nucleic acid sequence of SEQ ID NO: 2. The sequence set forth in SEQ ID NO: 1 includes a gene encoding a λCI protein, a linker amino acid sequence, a gene encoding an RIP140 protein and a FLAG sequence in the 5' to 3' direction, and the sequence set forth in SEQ ID NO: 2 includes a gene encoding an αNTD protein, a linker amino acid sequence, a gene encoding ER LBD and a FLAG sequence in the 5' to 3' direction.

In addition, when a TIF2 protein is used as a coregulatory factor, the plasmid A may have a nucleic acid sequence of SEQ ID NO: 3, and the plasmid B may have the nucleic acid sequence of SEQ ID NO: 2. The sequence set forth in SEQ ID NO: 3 includes a gene encoding a λCI protein, a linker amino acid sequence, a gene encoding a TIF2 protein and a FLAG sequence in the 5' to 3' direction, and the sequence set forth in SEQ ID NO: 2 includes a gene encoding an αNTD protein, a linker amino acid sequence, a gene encoding ER LBD and a FLAG sequence in the 5' to 3' direction.

The following examples will be described with reference to E. coli strains as cells transformed by the plasmids A and B according to the present invention, but the target strain is not limited to E. coli, and other than this, all of genetically-manipulated bacterial strains such as Bacillus subtilis, Bacillus licheniformis, lactic acid bacteria, etc. may be used as target strains.

In addition, the target compounds detected by the bacteria according to the present invention include all types of hormones and analogues which can bind to an estrogen receptor, as well as a human estrogen hormone. In the present invention, compounds, for example, various steroid-based hormones (norethynodrel, 5α-androstane, etc.), alkylphenol compounds (nonylphenol, dodecylphenol, octylphenol, etc.), bisphenol-type compounds (bisphenol A, bisphenol S, bisphenol F, etc.), paraben-based compounds generally used as a preservative (2-ethylhexyl 4-hydroxybenzoate, heptyl 4-hydroxybenzoate, etc.), benzophenone-based compounds used as a fixative for a cosmetic fragrance (4,4'-dihydroxybenzophenone, 2,4-dihydroxybenzophenone, etc.), organic chlorine-based substances contained in a pesticide (dihydroxymethoxychlorolefin, o,p'-DDT, dihydroxymethoxychlor (HPTE), 2',3',4',5'-tetrachloro-4-biphenylol, etc.), nordihydroguaiaretic acid also added to food as an antioxidant, aurin widely used as an acid-base indicator, compounds including phenolphthalein, phenol red, etc. may be detected, but the present invention is not limited thereto.

Furthermore, the present invention provides a method for detecting an estrogenic compound using the bacterial according to the present invention, the method including:

preparing bacterial strains according to the present invention;

culturing the bacterial strains by adding a specimen containing an estrogenic compound thereto; and lysing the culture bacterial strain and analyzing a degree of the expression of a reporter protein.

In other words, in the method according to the present invention, an estrogenic compound in a specimen may be analyzed by utilizing a characteristic of producing a specific protein by the bacteria according to the present invention only when the estrogenic compound, as a ligand, is present in the specimen and binds to ER LBD.

Therefore, in the method according to the present invention, first, the above-described bacterial strain transformed by the plasmids A and B is prepared and cultured with a specimen subjected to analysis, and after the cultured bacterial strain is lysed, a reporter protein expressed by the bacteria is analyzed. At this time, a reporter protein may be produced from a reporter gene only when an estrogenic compound is present in a specimen, and the produced reporter protein may be quantitatively analyzed, thereby detecting the estrogenic compound in the specimen.

In the present invention, a method for analyzing such a reporter protein may vary according to the type of expressed reporter protein, and for example, the reporter protein may be a β-galactosidase, a fluorescent protein or an antibiotic resistance-imparting protein, wherein the fluorescent protein may be a green fluorescent protein (GFP), a yellow fluorescent protein (YFP), a red fluorescent protein (RFP) or a luciferase. The colorimetric or fluorescent protein may be quantitatively analyzed using an instrument such as a UV-VIS spectrophotometer.

In addition, when a β-galactosidase is used as a reporter protein, the analysis may be performed by adding O-nitrophenyl-β-D-galactopyranoside (ONPG) as a colorimetric reagent after the lysis, and analyzing a degree of expression of the reporter protein. For example, when O-nitrophenyl-β-D-galactopyranoside (ONPG) is added as a colorimetric reagent, the added ONPG is degraded by a β-galactosidase, and orthonitrophenol exhibiting strong yellow emission is produced as a degradation product. At this time, a degree of yellow emission may vary according to the concentration of an estrogenic compound present in the specimen, and as the degree of the light emission caused by ONPG may be measured using an UV-VIS spectrophotometer, the concentration of an estrogenic compound present in the specimen can be quantitatively analyzed.

Hereinafter, the present invention will be described in further detail with reference to examples, and the following examples are merely provided to help in understanding the present invention, but the scope of the present invention is not limited thereto.

EXAMPLES

Example 1. Case of Using RIP140 Protein as Coregulatory Factor

Example 1-1. Construction of Plasmids

Full-length RIP140 was amplified by PCR using genomic DNA of a human breast cancer cell line MCF-7 as a template. In the amplification, a FLAG sequence was tagged to confirm protein expression using a specific antibody. hERα LBD ($N_{304}$-$T_{553}$: amino acid 304, asparagine, through amino acid 553, threonine) was amplified by PCR using DNA complementary to a human breast cancer cell line MCF-7 as a template, and as described above, in the amplification, a FLAG sequence was tagged. Specific conditions for PCR amplification are as follows.

A hERα LBD-FLAG gene was subjected to 30 repeated cycles of a reaction using an Ex-Taq DNA polymerase, sequentially under conditions of 95° C. for 1 minute, 95° C. for 30 seconds, 50° C. for 30 seconds, and 72° C. for 30 seconds. Afterward, finally, the reaction was performed at 72° C. for 5 minutes. For a RIP140-FLAG gene, a reaction was performed using the Ex-Taq DNA polymerase used in the above-described reaction. The reaction was repeated 30 cycles sequentially under conditions of 95° C. for 1 minute, 95° C. for 30 seconds, 50° C. for 30 seconds, and 72° C. for 2.5 minutes. Afterward, finally, the reaction was performed at 72° C. for 5 minutes.

The amplified RIP140-FLAG gene was cleaved with restriction enzymes such as Not I and Bgl II. Subsequently, the cleaved product was inserted into a pACλCI vector cleaved with Not I and BamH I using a ligase, thereby cloning a pACλCI:RIP140-FLAG plasmid (since, due to a BamH I site present in the middle of a RIP140 gene, a recognition sequence was different from that of BamH I, a different restriction enzyme Bgl II, which can bind to a part cleaved with BamH I was used). The amplified hERα LBD-FLAG sequence was also cleaved with Not I and BamH I, and inserted into pBRαNTD cleaved with Not I and BamH I using a ligase, thereby cloning a pBRαNTD::hERα LBD-FLAG sequence.

Example 1-2. Transformation of *E. coli*

First, competent cells of an *E. coli* strain, that is, *E. coli* FW102 OL2-62 (addgene) containing an F' plasmid in which a λCI operator is present at the lacZ reporter-62 position were constructed. Cells grown from $OD_{600}$ (optical density at 600 nm) to $OD_{0.4}$ were harvested. Afterward, the cells were treated with 100 mM $CaCl_2$ for approximately 4 hours, the treated cells were harvested, and then used after the cells were resuspended with 100 mM $CaCl_2$ at a volume corresponding to 1/50 of the medium volume used in the initial culture.

1 μL (approximately 100 ng) of each type of plasmid such as pACλCI::RIP140-FLAG and pBRαNTD::hERα LBD-FLAG (plasmids transferred to *E. coli* DH5α (cloning host) after cloning, amplified and then isolated again) was added to 50 μL of the prepared competent cells, and then stored at 0° C. for approximately 30 minutes. Afterward, after the cells were heated at 42° C. for 1 minute and 40 seconds, the cells were immediately stored at 0° C. for 5 minutes. Subsequently, 1 mL of an LB medium was added to the cells, the cells were cultured at 37° C. for 1 hour and then plated in a medium containing a selective marker such as kanamycin (F' plasmid selective), ampicillin (pBRαNTD::hERα LBD-FLAG selective), or chloramphenicol (pACλCI:: RIP140-FLAG selective).

Example 1-3. Analysis of β-Galactosidase

The *E. coli* FW102 OL2-62 pACλCI::RIP140-FLAG pBRαNTD::hERα LBD-FLAG strain was inoculated, and cultured up to $OD_{600 \sim}$ 0.4 (20 μM IPTG added; the inducible substance for inducing expression of λCI-RIP140-FLAG and αNTD-hERα LBD-FLAG). Afterward, estrogens and EDCs were added at corresponding concentrations, and the cells were further incubated for 30 minutes. Subsequently, 800 μL of the cells were harvested, and resuspended in 800 μL of a buffer solution (60 mM of $Na_2HPO_4$, 40 mM of $NaH_2PO_4$, 10 mM of KCl, 1 mM of $MgSO_4 7H_2O$, 400 μM of dithiothreitol), followed by measuring $OD_{600}$ (cell content). Afterward, the cells were lysed by ultrasonication and treated with 160 μL of 4 mg/mL ONPG, and thus a time to change a color of the specimen into yellow was recorded. When the color of the specimen changed to yellow, the reaction was stopped with 400 μL of 1M $Na_2CO_3$. Subsequently, $OD_{550}$ (cell debris) and $OD_{420}$ (intensity of yellow emission) were measured, and the activity was calculated according to the Miller Unit Formula $(1000*(((OD_{420}-(1.75*OD_{550}))/(t*v*OD_{600}))$.

FIGS. 2A and 2B show the results of confirming the ability of strains for detecting a representative estrogenic compound, 17β-estradiol. Since an estrogen receptor ligand-binding domain and a RIP140 protein are expressed by isopropyl 1-thio-β-D-galactoside (IPTG), it can be assumed that activity shown when IPTG was not added (-IPTG) is caused by an internal protein resulting from a strain itself. Therefore, as the activity shown when IPTG was not added (-IPTG) was subtracted from that shown when IPTG was added (+IPTG), only activity shown by a protein introduced though gene manipulation may be measured. Referring to FIGS. 2A and 2B, it can be confirmed that the higher the concentration of 17β-estradiol in a specimen, the higher the Miller units. Therefore, it can be seen that the *E. coli* according to the present invention is effectively used in measurement of the content of 17β-estradiol in a specimen.

In addition, FIG. 3 shows the result of confirming the ability of a strain according to the present invention for detecting different estrogenic compounds such as estriol and estrone, and referring to FIG. 3, like the results shown in FIGS. 2A and 2B, it can be seen that the Miller units increase in proportion to the concentration of an estrogenic compound in a specimen.

Furthermore, FIGS. 4A and 4B show the results of confirming the ability of strains according to the present invention for detecting representative environmental hormones such as bisphenol A and nonylphenol. Referring to FIG. 4, like the above-described results, it can be seen that the higher the concentration of an environmental hormone in a specimen, the higher the Miller units.

Finally, FIG. 5 shows the result of confirming the ability of a strain according to the present invention for detecting environmental hormones present in various articles which are available in daily life. A piece of each article with a size of 0.5 cm×0.5 cm (width×length) was immersed for 30 minutes during the culture of the strain and then removed, and undiluted shampoo was injected at 1/100 of the total volume of the cell culture. Referring to FIG. 5, it can be seen that the strain according to the present invention is able to be used in successfully detecting environmental hormones from various articles.

Example 2. Case of Using TIF2 Protein as Coregulatory Factor

Example 2-1. Construction of Plasmids

The binding domain of TIF2 (TIF2 BD ($Q_{624}$-$T_{869}$: amino acid 624, glutamine, through amino acid 869, threonine)) was amplified by Polymerase Chain Reaction (PCR) using DNA complementary to human breast cancer cells (MCF-7). During the amplification, a FLAG sequence was tagged to detect protein expression with a specific antibody. hERα LBD ($N_{304}$-T553: amino acid 304, asparagine, through amino acid 553, threonine) was amplified by PCR using DNA complementary to human breast cancer cells (MCF-7) as a template. As described above, during the amplification, a FLAG sequence was tagged.

The amplified TIF2 BD-FLAG gene was cleaved with restriction enzymes Not I and BamH I. Afterward, the cleaved product was ligated into a pACλCI vector cleaved with Not I and BamH I using a ligase, thereby cloning a pACλCI::TIF2 BD-FLAG plasmid. The amplified hERα LBD-FLAG was cleaved with Not I and BamH I. As described above, the cleaved product was ligated into pBRαNTD cleaved with Not I and BamH I using a ligase, thereby cloning a pBRαNTD::hERα LBD-FLAG plasmid.

Example 2-2. Transformation of E. coli

First, competent cells of an E. coli strain, that is, E. coli FW102 OL2-62 (addgene) containing an F' plasmid in which a λCI operator is present at the lacZ reporter-62 position were constructed. Cells grown from $OD_{600}$ (optical density at 600 nm) to $OD_{0.4}$ were harvested. Afterward, the cells were treated with 100 mM $CaCl_2$ for approximately 4 hours, the treated cells were harvested, and then used after the cells were resuspended with 100 mM $CaCl_2$ at a volume corresponding to 1/50 of the medium volume used in the initial culture.

1 µL (approximately 100 ng) of each type of plasmid such as pACλCI::RIP140-FLAG and pBRαNTD::hERα LBD-FLAG (plasmids transferred to E. coli DH5α (cloning host) after cloning, amplified and then isolated again) was added to 50 µL of the prepared competent cells, and then stored at 0° C. for approximately 30 minutes. Afterward, after the cells were heated at 42° C. for 1 minute and 40 seconds, the cells were immediately stored at 0° C. for 5 minutes. Subsequently, 1 mL of an LB medium was added to the cells, the cells were cultured at 37° C. for 1 hour and then plated in a medium containing a selective marker such as kanamycin (F' plasmid selective), ampicillin (pBRαNTD::hERα LBD-FLAG selective), or chloramphenicol (pACλCI::RIP140-FLAG selective).

Example 2-3. Analysis of β-Galactosidase

The E. coli FW102 OL2-62 pACλCI::TIF2 BD-FLAG pBRαNTD::hERα LBD-FLAG strain was inoculated, and cultured up to $OD_{600\sim}$ 0.4 (20 µM IPTG added; the inducible substance for inducing expression of λCI-TIF2 BD-FLAG and αNTD-hERα LBD-FLAG). Afterward, estrogens and EDCs were added at corresponding concentrations, and the cells were further incubated for 30 minutes. Subsequently, 800 µL of the cells were harvested, and resuspended in 800 µL of a buffer solution (60 mM of $Na_2HPO_4$, 40 mM of $NaH_2PO_4$, 10 mM of KCl, 1 mM of $MgSO_4 7H_2O$, 400 µM of dithiothreitol), followed by measuring $OD_{600}$ (cell content). Afterward, the cells were lysed by ultrasonication and treated with 160 µL of 4 mg/mL ONPG, and thus a time to change a color of the specimen into yellow was recorded. When the color of the specimen changed to yellow, the reaction was stopped with 400 µL of 1M $Na_2CO_3$. Subsequently, $OD_{550}$ (cell debris) and $OD_{420}$ (intensity of yellow emission) were measured, and the activity was calculated according to the Miller Unit Formula $(1000*(((OD_{420}-(1.75*OD_{550}))/(t*v*OD_{600}))$.

FIG. 6 shows the result of an experiment for comparing the sensitivities of LE7197 (sensor strain using TIF2: E. coli FW102 OL2-62 pBRαNTD::hERα LBD-FLAG pACλCI::TIF2 BD-FLAG) and LE7182 (sensor strain using RIP140: E. coli FW102 OL2-62 pBRαNTD::hERα LBD-FLAG pACλCI::RIP140-FLAG) according to the present invention with respect to a representative estrogen such as estradiol and a representative environmental hormone substance such as bisphenol A. The corresponding strains were cultured up to the exponential growth phase, and then treated with estradiol and bisphenol A at specific concentrations. Afterward, through β-galactosidase analysis, the expression of a reporter gene, the lacZ gene, was expressed in terms of Miller units. It was confirmed that LE7197 can sense 1 nM of estradiol and 1 µM of bisphenol A, and when treated with 10 nM of estradiol and 10 µM of bisphenol A, a signal-to-noise ratio increases 1.5 to 2 times higher than that of LE7182.

FIG. 7 shows the result of an experimental for confirming the estradiol detecting ability of a sensor strain (LE7197) into which a TIF2 protein is introduced as a coregulatory factor interacting with ER LBD according to the present invention. IPTG serves to express a fusion protein of RNA polymerase αNTD-estrogen receptor protein ligand-binding domain and a fusion protein of λCI-TIF2 binding site proteins in a strain. When IPTG is not treated, the expression of the lacZ gene does not occur even with the treatment of an estrogen. When a slightly higher concentration of estrogen is treated, low sensitivity occurs due to leaky expression of the protein. In the presence of IPTG, the higher the concentration of an estrogen, the higher the intensity of a signal, which indicates that even 1 nM of an estrogen can be detected.

FIG. 8 shows the result of an experiment for confirming sensitivity of a sensor strain (LE7197) using a TIF2 protein as a coregulatory factor interacting with ER LBD according to the present invention with respect to various concentrations of estrone and estriol. It was confirmed that approximately several nM of an estrogen can be detected.

FIG. 9 shows the result of an experiment for confirming the sensibility of a sensor strain (LE7197) using a TIF2 protein as a coregulatory factor interacting with ER LBD according to the present invention with respect to various concentrations of bisphenol A and nonylphenol. It was confirmed that approximately 1 µM of bisphenol A and approximately 100 nM of nonylphenol can be detected.

FIG. 10 shows the result of an experiment for confirming the sensibility of a sensor strain (LE7197) using a TIF2 protein as a coregulatory factor interacting with ER LBD according to the present invention with respect to various concentrations of bisphenol S and bisphenol F. It can be confirmed that the strains according to the present invention can sense several hundred nM of bisphenol S and bisphenol F, which have been widely used as alternatives for bisphenol A in recent years.

In conclusion, the bacterial strain having a detecting ability of an estrogenic compound and the method for detecting an estrogenic compound using the same according to the present invention can detect estrogenic compounds from various specimens in a very short time by a relatively simple process.

INDUSTRIAL APPLICABILITY

The present invention can detect an estrogenic compound using a genetically-modified bacterial strain, and since the present invention is based on a human-derived estrogen receptor protein, the detection can be performed in a very short time with a low cost and a low amount of labor according to an eco-friendly, relatively simple process, and thus can be applied in food, medical and environmental industries, requiring detection of an estrogenic compound.

The invention claimed is:

1. A bacterial strain having an ability of detecting an estrogenic compound, the strain comprising:
    plasmid A comprising a nucleotide sequence encoding a coregulatory factor protein conjugated with a nucleotide sequence encoding a λCI protein,
    wherein said coregulatory factor protein is capable of binding an estrogen receptor ligand-binding domain (ER LBD) when said ER LBD is bound to an estrogenic compound; and
    plasmid B comprising a nucleotide sequence encoding the ER LBD conjugated with a nucleotide sequence encoding an α subunit N-terminal domain (αNTD) protein,
    wherein the nucleotide sequence encoding the coregulatory factor protein is a nucleotide sequence corresponding to nucleotides at positions 2350 to 5826 in SEQ ID NO: 1 or 2350 to 3090 in SEQ ID NO: 3; the nucleotide sequence encoding the λCI protein is a nucleotide sequence corresponding to nucleotides at positions 1630 to 2348 in SEQ ID NO: 1 and SEQ ID NO: 3; the nucleotide sequence encoding the ER LBD is a nucleotide sequence corresponding to nucleotides at positions 1112 to 1861 in SEQ ID NO: 2; and the nucleotide sequence encoding the αNTD protein is a nucleotide sequence corresponding to nucleotides at positions 359 to 1110 in SEQ ID NO: 2.

2. The bacterial strain according to claim 1, wherein the bacterial strain is any one strain selected from the group comprising *Escherichia coli, Bacillus subtilis, Bacillus licheniformis* and lactic acid bacteria.

3. The bacterial strain according to claim 1, wherein the estrogenic compound is selected from the group comprising norethynodrel, 5α-androstane, nonylphenol, dodecylphenol, octylphenol, bisphenol A, bisphenol S, bisphenol F, 2-ethylhexyl-4-hydroxybenzoate, 4,4'-dihyroxybenzophenone, 2,4-dihydroxybenzophenone, dihydroxymethoxychlorolefin, o,p'-DDT, dihydroxymethoxychlor (HPTE), 2',3',4',5'-tetrachloro-4-biphenylol, nordihydroguaiaretic acid, aurin, phenolphthalein, phenol red, and a mixture thereof.

4. A method for detecting an estrogenic compound, comprising:
    providing the bacterial strain having an ability of detecting an estrogenic compound of claim 1;
    culturing the bacterial strain to which a specimen containing an estrogenic compound is added; and
    lysing the culture bacterial strain and analyzing a degree of the expression of a reporter protein.

5. The method according to claim 4, wherein the reporter protein is a β-galactosidase, a fluorescent protein or an antibiotic resistance-imparting protein.

6. The method according to claim 5, wherein the fluorescent protein is a green fluorescent protein (GFP), a yellow fluorescent protein (YFP), a red fluorescent protein (RFP) or a luciferase.

7. The method according to claim 4, wherein the degree of the expression of a reporter protein is analyzed using a UV-VIS spectrophotometer.

8. The method according to claim 4, wherein the degree of the expression of the β-galactosidase is measured by adding O-nitrophenyl-β-D-galactopyranoside (ONPG) as a colorimetric reagent after the lysis, and analyzing the expression degree.

9. The bacterial strain according to claim 1, wherein the plasmid A comprises the nucleic acid nucleotide sequence of SEQ ID NO: 1 or 3 and the plasmid B comprises the nucleotide sequence of SEQ ID NO: 2.

10. The bacterial strain according to claim 1, wherein a polypeptide tag encoded by the nucleotide sequence corresponding to nucleotides at positions 1862 to 1885 in SEQ ID NO: 2 is conjugated to the 3'-end of the nucleotide sequence encoding the ER LBD.

* * * * *

SEQUENCE LISTING

<160> NUMBER OF SEQ ID NOS: 3

<210> SEQ ID NO 1
<211> LENGTH: 6670
<212> TYPE: DNA
<213> ORGANISM: Artificial
<220> FEATURE:
<223> OTHER INFORMATION: Plasmid A

<400> SEQUENCE: 1

| | | | | | |
|---|---|---|---|---|---|
| gaattccgga | tgagcattca | tcaggcgggc | aagaatgtga | ataaaggccg | gataaaactt | 60 |
| gtgcttattt | ttctttacgg | tctttaaaaa | ggccgtaata | tccagctgaa | cggtctggtt | 120 |
| ataggtacat | tgagcaactg | actgaaatgc | ctcaaaatgt | tctttacgat | gccattggga | 180 |
| tatatcaacg | gtggtatatc | cagtgatttt | tttctccatt | ttagcttcct | tagctcctga | 240 |
| aaatctcgat | aactcaaaaa | atacgcccgg | tagtgatctt | atttcattat | ggtgaaagtt | 300 |
| ggaacctctt | acgtgccgat | caacgtctca | ttttcgccaa | aagttggccc | agggcttccc | 360 |
| ggtatcaaca | gggacaccag | gatttattta | ttctgcgaag | tgatcttccg | tcacaggtat | 420 |
| ttattcggcg | caaagtgcgt | cgggtgaatg | ctgccaactt | actgattagt | gtatgatggt | 480 |
| gtttttgagg | tgctccagtg | gcttctgttt | ctatcagctg | tccctcctgt | tcagctactg | 540 |
| acggggtggt | gcgtaacggc | aaaagcaccg | ccggacatca | gcgctagcgg | agtgtatact | 600 |
| ggcttactat | gttggcactg | atgagggtgt | cagtgaagtg | cttcatgtgg | caggagaaaa | 660 |
| aaggctgcac | cggtgcgtca | gcagaatatg | tgatacagga | tatattccgc | ttcctcgctc | 720 |
| actgactcgc | tacgctcggt | cgttcgactg | cggcgagcgg | aaatggctta | cgaacggggc | 780 |
| ggagatttcc | tggaagatgc | caggaagata | cttaacaggg | aagtgagagg | gccgcggcaa | 840 |
| agccgttttt | ccataggctc | cgcccccctg | acaagcatca | cgaaatctga | cgctcaaatc | 900 |
| agtggtggcg | aaacccgaca | ggactataaa | gataccaggc | gtttccctg | gcggctccct | 960 |
| cgtgcgctct | cctgttcctg | cctttcggtt | taccggtgtc | attccgctgt | tatggccgcg | 1020 |
| tttgtctcat | tccacgcctg | acactcagtt | ccgggtaggc | agttcgctcc | aagctggact | 1080 |
| gtatgcacga | accccccgtt | cagtccgacc | gctgcgcctt | atccggtaac | tatcgtcttg | 1140 |
| agtccaaccc | ggaaagacat | gcaaaagcac | cactggcagc | agccactggt | aattgattta | 1200 |
| gaggagttag | tcttgaagtc | atgcgccggt | taaggctaaa | ctgaaaggac | aagttttggt | 1260 |
| gactgcgctc | ctccaagcca | gttacctcgg | ttcaaagagt | tggtagctca | gagaaccttc | 1320 |
| gaaaaaccgc | cctgcaaggc | ggttttttcg | ttttcagagc | aagagattac | gcgcagacca | 1380 |
| aaacgatctc | aagaagatca | tcttattaat | cagataaaat | atttctagat | ttcagtgcaa | 1440 |
| tttatctctt | caaatgtagc | acctgaagtc | agccccatac | gatataagtt | gtaattctca | 1500 |
| tgtttgacag | cttatcatcg | ataagctaat | tctcactcat | taggcacccc | aggctttaca | 1560 |
| ctttatgctt | ccggctcgta | taatgtgtgg | aattgtgagc | ggataacaat | ttcacacagg | 1620 |
| aaacagcgta | tgagcacaaa | aaagaaacca | ttaacacaag | agcagcttga | ggacgcacgt | 1680 |
| cgccttaaag | caatttatga | aaaaagaaa | aatgaacttg | gcttatccca | ggaatctgtc | 1740 |
| gcagacaaga | tggggatggg | gcagtcaggc | gttggtgctt | tatttaatgg | catcaatgca | 1800 |
| ttaaatgctt | ataacgccgc | attgcttgca | aaaattctca | agttagcgt | tgaagaattt | 1860 |
| agcccttcaa | tcgccagaga | aatctacgag | atgtatgaag | cggttagtat | gcagccgtca | 1920 |
| cttagaagtg | agtatgagta | ccctgttttt | tctcatgttc | aggcagggat | gttctcacct | 1980 |
| gagcttagaa | cctttaccaa | aggtgatgcg | gagagatggg | taagcacaac | caaaaaagcc | 2040 |

```
agtgattctg cattctggct tgaggttgaa ggtaattcca tgaccgcacc aacaggctcc    2100
aagccaagct ttcctgacgg aatgttaatt ctcgttgacc ctgagcaggc tgttgagcca    2160
ggtgatttct gcatagccag acttgggggt gatgagttta ccttcaagaa actgatcagg    2220
gatagcggtc aggtgttttt acaaccacta aacccacagt acccaatgat cccatgcaat    2280
gagagttgtt ccgttgtggg gaaagttatc gctagtcagt ggcctgaaga gacgtttggc    2340
gcggccgcaa tgactcatgg agaagagctt ggctctgatg tgcaccagga ttctattgtt    2400
ttaacttacc tagaaggatt actaatgcat caggcagcag ggggatcagg tactgccgtt    2460
gacaaaaagt ctgctgggca taatgaagag gatcagaact ttaacatttc tggcagtgca    2520
tttcccacct gtcaaagtaa tggtccagtt ctcaatacac atacatatca ggggtctggc    2580
atgctgcacc tcaaaaaagc cagactgttg cagtcttctg aggactggaa tgcagcaaag    2640
cggaagaggc tgtctgattc tatcatgaat ttaaacgtaa agaaggaagc tttgctagct    2700
ggcatggttg acagtgtgcc taaaggcaaa caggatagca cattactggc ctctttgctt    2760
cagtcattca gctctaggct gcagactgtt gctctgtcac aacaaatcag gcagagcctc    2820
aaggagcaag gatatgccct cagtcatgat tcttaaaag tggagaagga tttaaggtgc    2880
tatggtgttg catcaagtca cttaaaaact ttgttgaaga aaagtaaagt taaagatcaa    2940
aagcctgata cgaatcttcc tgatgtgact aaaaacctca tcagagatag gtttgcagag    3000
tctcctcatc atgttggaca aagtggaaca aaggtcatga gtgaaccgtt gtcatgtgct    3060
gcaagattac aggctgttgc aagcatggtg gaaaaaggg ctagtcctgc cacctcacct    3120
aaacctagtg ttgcttgtag ccagttagca ttacttctgt caagcgaagc ccatttgcag    3180
cagtattctc gagaacacgc tttaaaaacg caaaatgcaa atcaagcagc aagtgaaaga    3240
cttgctgcta tggccagatt gcaagaaaat ggccagaagg atgttggcag ttaccagctc    3300
ccaaaaggaa tgtcaagcca tcttaatggt caggcaagaa catcatcaag caaactgatg    3360
gctagcaaaa gtagtgctac agtgtttcaa aatccaatgg gtatcattcc ttcttcccct    3420
aaaaatgcag gttataagaa ctcactggaa agaaacaata taaaacaagc tgctaacaat    3480
agtttgcttt tacatcttct aaaagccag actataccta agccaatgaa tggacacagt    3540
cacagtgaga gaggaagcat ttttgaggaa agtagtacac ctacaactat tgatgaatat    3600
tcagataaca atcctagttt tacagatgac agcagtggtg atgaaagttc ttattccaac    3660
tgtgttccca tagacttgtc ttgcaaacac cgaactgaaa aatcagaatc tgaccaacct    3720
gtttccctgg ataacttcac tcaatccttg ctaaacactt gggatccaaa agtcccagat    3780
gtagatatca aagaagatca agataccctca aagaattcta agctaaactc acaccagaaa    3840
gtaacacttc ttcaattgct acttggccat aagaatgaag aaaatgtaga aaaaacacc    3900 agccctcagg gagtacacaa tgatgtgagc aagttcaata cacaaaatta tgcaaggact    3960
tctgtgatag aaagcccag tacaaatcgg actactccag tgagcactcc acctttactt    4020
acatcaagca aagcagggtc tcccatcaat ctctctcaac actctctggt catcaaatgg    4080
aattccccac catatgtctg cagtactcag tctgaaaagc taacaaatac tgcatctaac    4140
cactcaatgg accttacaaa aagcaaagac ccaccaggag agaaaccagc ccaaaatgaa    4200
ggtgcacaga actctgcaac gtttagtgcc agtaagctgt tacaaaattt agcacaatgt    4260
ggaatgcagt catccatgtc agtggaagag cagagaccca gcaaacagct gttaactgga    4320
aacacagata aaccgatagg tatgattgat agattaaata gcccttttgct ctcaaataaa    4380
```

-continued

```
acaaatgcag ttgaagaaaa taaagcattt agtagtcaac caacaggtcc tgaaccaggg    4440
ctttctggtt ctgaaataga aaatctgctt gaaagacgta ctgtcctcca gttgctcctg    4500
gggaacccca acaaagggaa gagtgaaaaa aaagagaaaa ctcccttaag agatgaaagt    4560
actcaggaac actcagagag agctttaagt gaacaaatac tgatggtgaa aataaaatct    4620
gagccttgtg atgacttaca aattcctaac acaaatgtgc acttgagcca tgatgctaag    4680
agtgccccat tcttgggtat ggctcctgct gtgcagagaa gcgcacctgc cttaccagtg    4740
tccgaagact ttaaatcgga gcctgtttca cctcaggatt tttctttctc caagaatggt    4800
ctgctaagtc gattgctaag acaaaatcaa gatagttacc tggcagatga ttcagacagg    4860
agtcacagaa ataatgaaat ggcacttcta gaatcaaaga atctttgcat ggtccctaag    4920
aaaaggaagc tttatactga gccattagaa aatccattta aaagatgaa aaacaacatt     4980 gttgatgctg caaacaatca cagtgcccca gaagtactgt atgggtcctt gcttaaccag    5040
gaagagctga atttagcag aaatgatctt gaatttaaat atcctgctgg tcatggctca    5100
gccagcgaaa gtgaacacag gagttgggcc agagagagca aaagctttaa tgttctgaaa    5160
cagctgcttc tctcagaaaa ctgtgtgcga gatttgtccc cgcacagaag taactctgtg    5220
gctgacagta aaagaaagg acacaaaaat aatgtgacca cagcaaacc tgaatttagc      5280 atttcttctt taaatggact gatgtacagt tccactcagc ccagcagttg catggataac    5340
aggacatttt catacccagg tgtagtaaaa actcctgtga gtcctacttt ccctgagcac    5400
ttgggctgtg cagggtctag accagaatct gggcttttga atgggtgttc catgcccagt    5460
gagaaaggac ccattaagtg ggttatcact gatgcggaga agaatgagta tgaaaaagac    5520
tctccaagat tgaccaaaac caacccaata ctatattaca tgcttcaaaa aggaggcaat    5580
tctgttacca gtcgagaaac acaagacaag gacatttgga gggaggcttc atctgctgaa    5640
agtgtctcac aggtcacagc caaagaagag ttacttccta ctgcagaaac gaaagcttct    5700
ttctttaatt taagaagccc ttacaatagc catatgggaa ataatgcttc tcgcccacac    5760
agcgcaaatg gagaagttta tggacttctg ggaagcgtgc taacgataaa gaaagaatca    5820
gaagattata aagatgatga tgataaataa agatccttac cttacagatc tgcatcgcag    5880
gatgctgctg gctaccctgt ggaacaccta catctgtatt aacgaagcgc taaccgtttt    5940
tatcaggctc tgggaggcag aataaatgat catatcgtca attattacct ccacggggag    6000
agcctgagca aactggcctc aggcatttga gaagcacacg gtcacactgc ttccggtagt    6060
caataaaccg gtaaaccagc aatagacata agcggctatt taacgaccct gccctgaacc    6120
gacgaccggg tcgaatttgc tttcgaattt ctgccattca tccgcttatt atcacttatt    6180
caggcgtagc accaggcgtt taagggcacc aataactgcc ttaaaaaat tacgccccgc     6240 cctgccactc atcgcagtac tgttgtaatt cattaagcat tctgccgaca tggaagccat    6300
cacagacggc atgatgaacc tgaatcgcca gcggcatcag caccttgtcg ccttgcgtat    6360
aatatttgcc catggtgaaa acggggggcga agaagttgtc catattggcc acgtttaaat    6420
caaaactggt gaaactcacc cagggattgg ctgagacgaa aaacatattc tcaataaacc    6480
ctttagggaa ataggccagg ttttcaccgt aacacgccac atcttgcgaa tatatgtgta    6540
gaaactgccg gaaatcgtcg tggtattcac tccagagcga tgaaaacgtt tcagtttgct    6600
catggaaaac ggtgtaacaa gggtgaacac tatcccatat caccagctca ccgtctttca    6660
ttgccatacg                                                           6670
```

<210> SEQ ID NO 2
<211> LENGTH: 5874
<212> TYPE: DNA
<213> ORGANISM: Artificial
<220> FEATURE:
<223> OTHER INFORMATION: Plasmid B

<400> SEQUENCE: 2

| | | | | | |
|---|---|---|---|---|---|
| gcaataaaaa | atcaaatcgg | atttcactat | ataatctcac | tttatctaag | atgaatccga | 60 |
| tggaagcatc | ctgttttctc | tcaattttt | tatctaaaac | ccagcgttcg | atgcttcttt | 120 |
| gagcgaacga | tcaaaaataa | gtgccttccc | atcaaaaaaa | tattgacaac | ataaaaaact | 180 |
| ttgtgttata | cttgtaacgc | tacatggaga | ttaactcaat | ctagctagag | aggctttaca | 240 |
| ctttatgctt | ccggctcgta | taatgtgtgg | aattgtgagc | ggataacaat | ttcacacagg | 300 |
| aaacagctat | gaccatgatt | acggattcac | tggaactcta | gaccaaagag | aggacacaat | 360 |
| gcagggttct | gtgacagagt | ttctaaaacc | gcgcctggtt | gatatcgagc | aagtgagttc | 420 |
| gacgcacgcc | aaggtgaccc | ttgagccttt | agagcgtggc | tttggccata | ctctgggtaa | 480 |
| cgcactgcgc | cgtattctgc | tctcatcgat | gccgggttgc | gcggtgaccg | aggttgagat | 540 |
| tgatggtgta | ctacatgagt | acagcaccaa | agaaggcgtt | caggaagata | tcctggaaat | 600 |
| cctgctcaac | ctgaaagggc | tggcggtgag | agttcagggc | aaagatgaag | ttattcttac | 660 |
| cttgaataaa | tctggcattg | ccctgtgac | tgcagccgat | atcacccacg | acggtgatgt | 720 |
| cgaaatcgtc | aagccgcagc | acgtgatctg | ccacctgacc | gatgagaacg | cgtctattag | 780 |
| catgcgtatc | aaagttcagc | gcggtcgtgg | ttatgtgccg | gcttctaccc | gaattcattc | 840 |
| ggaagaagat | gagcgcccaa | tcggccgtct | gctggtcgac | gcatgctaca | gccctgtgga | 900 |
| gcgtattgcc | tacaatgttg | aagcagcgcg | tgtagaacag | cgtaccgacc | tggacaagct | 960 |
| ggtcatcgaa | atggaaacca | acggcacaat | cgatcctgaa | gaggcgattc | gtcgtgcggc | 1020 |
| aaccattctg | gctgaacaac | tggaagcttt | cgttgactta | cgtgatgtac | gtcagcctga | 1080 |
| agtgaaagaa | gagaaaccag | aggcggccgc | aaacagcctg | gccttgtccc | tgacggccga | 1140 |
| ccagatggtc | agtgccttgt | tggatgctga | gccccccata | ctctattccg | agtatgatcc | 1200 |
| taccagaccc | ttcagtgaag | cttcgatgat | gggcttactg | accaacctgg | cagacaggga | 1260 |
| gctggttcac | atgatcaact | gggcgaagag | ggtgccaggc | tttgtggatt | tgacccctca | 1320 |
| tgatcaggtc | caccttctag | aatgtgcctg | gctagagatc | ctgatgattg | gtctcgtctg | 1380 |
| gcgctccatg | gagcacccag | ggaagctact | gtttgctcct | aacttgctct | tggacaggaa | 1440 |
| ccagggaaaa | tgtgtagagg | gcatggtgga | gatcttcgac | atgctgctgg | ctacatcatc | 1500 |
| tcggttccgc | atgatgaatc | tgcagggaga | ggagtttgtg | tgcctcaaat | ctattatttt | 1560 |
| gcttaattct | ggagtgtaca | catttctgtc | cagcacctg | aagtctctgg | aagagaagga | 1620 |
| ccatatccac | cgagtcctgg | acaagatcac | agacactttg | atccacctga | tggccaaggc | 1680 |
| aggcctgacc | ctgcagcagc | agcaccagcg | gctgccccag | ctcctcctca | tcctctccca | 1740 |
| catcaggcac | atgagtaaca | aaggcatgga | gcatctgtac | agcatgaagt | gcaagaacgt | 1800 |
| ggtgccctc | tatgacctgc | tgctggagat | gctggacgcc | caccgcctac | atgcgcccac | 1860 |
| tgattataaa | gatgatgatg | ataaataagg | atcctctacg | ccggacgcat | cgtggccggc | 1920 |
| atcaccggcg | ccacaggtgc | ggttgctggc | gcctatatcg | ccgacatcac | cgatggggaa | 1980 |
| gatcgggctc | gccacttcgg | gctcatgagc | gcttgtttcg | gcgtgggtat | ggtggcaggc | 2040 |
| cccgtggccg | ggggactgtt | gggcgccatc | tccttgcatg | caccattcct | tgcggcggcg | 2100 |

-continued

```
gtgctcaacg gcctcaacct actactgggc tgcttcctaa tgcaggagtc gcataaggga      2160
gagcgtcgac cgatgccctt gagagccttc aacccagtca gctccttccg gtgggcgcgg      2220
ggcatgacta tcgtcgccgc acttatgact gtcttcttta tcatgcaact cgtaggacag      2280
gtgccggcag cgctctgggt cattttcggc gaggaccgct ttcgctggag cgcgacgatg      2340
atcggcctgt cgcttgcggt attcggaatc ttgcacgccc tcgctcaagc cttcgtcact      2400
ggtcccgcca ccaaacgttt cggcgagaag caggccatta tcgccggcat ggcggccgac      2460
gcgctgggct acgtcttgct ggcgttcgcg acgcgaggct ggatggcctt ccccattatg      2520
attcttctcg cttccggcgg catcgggatg cccgcgttgc aggccatgct gtccaggcag      2580
gtagatgacg accatcaggg acagcttcaa ggatcgctcg cggctcttac cagcctaact      2640
tcgatcactg gaccgctgat cgtcacggcg atttatgccg cctcggcgag cacatggaac      2700
gggttggcat ggattgtagg cgccgcccta taccttgtct gcctccccgc gttgcgtcgc      2760
ggtgcatgga gccgggccac ctcgacctga atggaagccg gcggcacctc gctaacggat      2820
tcaccactcc aagaattgga gccaatcaat tcttgcggag aactgtgaat gcgcaaacca      2880
acccttggca gaacatatcc atcgcgtccg ccatctccag cagccgcacg cggcgcatct      2940
cgggcagcgt tgggtcctgg ccacgggtgc gcatgatcgt gctcctgtcg ttgaggaccc      3000
ggctaggctg gcggggttgc cttactggtt agcagaatga atcaccgata cgcgagcgaa      3060
cgtgaagcga ctgctgctgc aaaacgtctg cgacctgagc aacaacatga atggtcttcg      3120
gtttccgtgt ttcgtaaagt ctggaaacgc ggaagtcagc gccctgcacc attatgttcc      3180
ggatctgcat cgcaggatgc tgctggctac cctgtggaac acctacatct gtattaacga      3240
agcgctggca ttgaccctga gtgattttc tctggtcccg ccgcatccat accgccagtt      3300
gtttaccctc acaacgttcc agtaaccggg catgttcatc atcagtaacc cgtatcgtga      3360
gcatcctctc tcgtttcatc ggtatcatta ccccatgaa cagaaatccc ccttacacgg       3420
aggcatcagt gaccaaacag gaaaaaaccg cccttaacat ggcccgcttt atcagaagcc      3480
agacattaac gcttctggag aaactcaacg agctggacgc ggatgaacag gcagacatct      3540
gtgaatcgct tcacgaccac gctgatgagc tttaccgcag ctgcctcgcg cgtttcggtg      3600
atgacggtga aaacctctga cacatgcagc tcccggagac ggtcacagct tgtctgtaag      3660
cggatgccgg gagcagacaa gcccgtcagg gcgcgtcagc gggtgttggc gggtgtcggg      3720
gcgcagccat gacccagtca cgtagcgata gcggagtgta tactggctta actatgcggc      3780
atcagagcag attgtactga gagtgcacca tatgcggtgt gaaataccgc acagatgcgt      3840
aaggagaaaa taccgcatca ggcgctcttc cgcttcctcg ctcactgact cgctgcgctc      3900
ggtcgttcgg ctgcggcgag cggtatcagc tcactcaaag gcggtaatac ggttatccac      3960
agaatcaggg gataacgcag gaaagaacat gtgagcaaaa ggccagcaaa aggccaggaa      4020
ccgtaaaaag gccgcgttgc tggcgttttt ccataggctc cgcccccctg acgagcatca      4080
caaaaatcga cgctcaagtc agaggtggcg aaacccgaca ggactataaa gataccaggc      4140
gtttccccct ggaagctccc tcgtgcgctc tcctgttccg accctgccgc ttaccggata      4200
cctgtccgcc tttctccctt cgggaagcgt ggcgctttct catagctcac gctgtaggta      4260
tctcagttcg gtgtaggtcg ttcgctccaa gctgggctgt gtgcacgaac cccccgttca      4320
gcccgaccgc tgcgccttat ccggtaacta tcgtcttgag tccaacccgg taagacacga      4380
cttatcgcca ctggcagcag ccactggtaa caggattagc agagcgaggt atgtaggcgg      4440
tgctacagag ttcttgaagt ggtggcctaa ctacggctac actagaagga cagtatttgg      4500
```

```
tatctgcgct ctgctgaagc cagttacctt cggaaaaaga gttggtagct cttgatccgg    4560
caaacaaacc accgctggta gcggtggttt tttgtttgc aagcagcaga ttacgcgcag    4620 aaaaaagga tctcaagaag atcctttgat cttttctacg gggtctgacg ctcagtggaa    4680
cgaaaactca cgttaaggga ttttggtcat gagattatca aaaaggatct tcacctagat    4740
ccttttaaat taaaaatgaa gttttaaatc aatctaaagt atatatgagt aaacttggtc    4800
tgacagttac caatgcttaa tcagtgaggc acctatctca gcgatctgtc tatttcgttc    4860
atccatagtt gcctgactcc ccgtcgtgta gataactacg atacgggagg gcttaccatc    4920
tggccccagt gctgcaatga taccgcgaga cccacgctca ccggctccag atttatcagc    4980
aataaaccag ccagccggaa gggccgagcg cagaagtggt cctgcaactt tatccgcctc    5040
catccagtct attaattgtt gccgggaagc tagagtaagt agttcgccag ttaatagttt    5100
gcgcaacgtt gttgccattg ctgcaggcat cgtggtgtca cgctcgtcgt ttggtatggc    5160
ttcattcagc tccggttccc aacgatcaag gcgagttaca tgatccccca tgttgtgcaa    5220
aaaagcggtt agctccttcg gtcctccgat cgttgtcaga agtaagttgg ccgcagtgtt    5280
atcactcatg gttatggcag cactgcataa ttctcttact gtcatgccat ccgtaagatg    5340
cttttctgtg actggtgagt actcaaccaa gtcattctga atagtgta tgcggcgacc    5400 gagttgctct tgcccggcgt caacacggga taataccgcg ccacatagca gaactttaaa    5460
agtgctcatc attggaaaac gttcttcggg gcgaaaactc tcaaggatct taccgctgtt    5520
gagatccagt tcgatgtaac ccactcgtgc acccaactga tcttcagcat cttttacttt    5580
caccagcgtt tctgggtgag caaaaacagg aaggcaaaat gccgcaaaaa agggaataag    5640
ggcgacacgg aaatgttgaa tactcatact cttcctttt caatattatt gaagcattta    5700
tcagggttat tgtctcatga gcggatacat atttgaatgt atttagaaaa ataaacaaat    5760
agggggtccg cgcacatttc cccgaaaagt gccacctgac gtctaagaaa ccattattat    5820
catgacatta acctataaaa ataggcgtat cacgaggccc tttggataac caga          5874
```

<210> SEQ ID NO 3
<211> LENGTH: 3934
<212> TYPE: DNA
<213> ORGANISM: Artificial
<220> FEATURE:
<223> OTHER INFORMATION: Plasmid A
<400> SEQUENCE: 3

```
gaattccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga     240
aaatctcgat aactcaaaaa atacgcccgg tagtgatctt atttcattat ggtgaaagtt     300
ggaacctctt acgtgccgat caacgtctca ttttcgccaa aagttggccc agggcttccc     360
ggtatcaaca gggacaccag gatttattta ttctgcgaag tgatcttccg tcacaggtat     420
ttattcggcg caaagtgcgt cgggtgaatg ctgccaactt actgattagt gtatgatggt     480 gttttgagg tgctccagtg gcttctgttt ctatcagctg tccctcctgt tcagctactg     540
acggggtggt gcgtaacggc aaaagcaccg ccggacatca gcgctagcgg agtgtatact     600
ggcttactat gttggcactg atgagggtgt cagtgaagtg cttcatgtgg caggagaaaa     660
```

```
aaggctgcac cggtgcgtca gcagaatatg tgatacagga tatattccgc ttcctcgctc    720
actgactcgc tacgctcggt cgttcgactg cggcgagcgg aaatggctta cgaacggggc    780
ggagatttcc tggaagatgc caggaagata cttaacaggg aagtgagagg ccgcggcaa     840 agccgttttt ccataggctc cgccccctg acaagcatca cgaaatctga cgctcaaatc     900
agtggtggcg aaacccgaca ggactataaa gataccaggc gtttccctg gcggctccct     960 cgtgcgctct cctgttcctg cctttcggtt taccggtgtc attccgctgt tatggccgcg    1020
tttgtctcat tccacgcctg acactcagtt ccgggtaggc agttcgctcc aagctggact    1080
gtatgcacga ccccccgtt cagtccgacc gctgcgcctt atccggtaac tatcgtcttg     1140
agtccaaccc ggaaagacat gcaaaagcac cactggcagc agccactggt aattgattta    1200
gaggagttag tcttgaagtc atgcgccggt taaggctaaa ctgaaaggac aagttttggt    1260
gactgcgctc ctccaagcca gttacctcgg ttcaaagagt tggtagctca gagaaccttc    1320 gaaaaccgc cctgcaaggc ggttttttcg ttttcagagc aagagattac gcgcagacca     1380
aaacgatctc aagaagatca tcttattaat cagataaaat atttctagat ttcagtgcaa    1440
tttatctctt caaatgtagc acctgaagtc agccccatac gataagtt gtaattctca      1500 tgtttgacag cttatcatcg ataagctaat tctcactcat taggcacccc aggctttaca    1560
ctttatgctt ccggctcgta taatgtgtgg aattgtgagc ggataacaat ttcacacagg    1620
aaacagcgta tgagcacaaa aagaaacca ttaacacaag agcagcttga ggacgcacgt     1680
cgccttaaag caatttatga aaaaagaaa atgaacttg gcttatccca ggaatctgtc      1740
gcagacaaga tggggatggg gcagtcaggc gttggtgctt tatttaatgg catcaatgca    1800
ttaaatgctt ataacgccgc attgcttgca aaaattctca agttagcgt tgaagaattt     1860 agcccttcaa tcgccagaga aatctacgag atgtatgaag cggttagtat gcagccgtca    1920
cttagaagtg agtatgagta ccctgttttt tctcatgttc aggcagggat gttctcacct    1980
gagcttagaa ccttaccaa aggtgatgcg gagagatggg taagcacaac caaaaaagcc     2040
agtgattctg cattctggct tgaggttgaa ggtaattcca tgaccgcacc aacaggctcc    2100
aagccaagct ttcctgacgg aatgttaatt ctcgttgacc ctgagcaggc tgttgagcca    2160
ggtgatttct gcatagccag acttgggggt gatgagttta ccttcaagaa actgatcagg    2220
gatagcggtc aggtgttttt acaaccacta aacccacagt acccaatgat ccatgcaat     2280 gagagttgtt ccgttgtggg gaaagttatc gctagtcagt ggcctgaaga gacgtttggc    2340
gcggccgcag agagagctga cgggcagagc agactgcatg acagcaaagg gcagaccaaa    2400
ctcctgcagc tgctgaccac caaatctgat cagatggagc cctcgccctt agccagctct    2460
ttgtcggata caaacaaaga ctccacaggt agcttgcctg ttctgggtc tacacatgga     2520 acctcgctca aggagaagca taaaattttg cacagactct gcaggacag cagttcccct    2580 gtggacttgg ccaagttaac agcagaagcc acaggcaaag acctgagcca ggagtccagc    2640
agcacagctc ctggatcaga agtgactatt aaacaagagc cggtgagccc caagaagaaa    2700
gagaatgcac tacttcgcta tttgctagat aaagatgata ctaaagatat tggtttacca    2760
gaaataaccc ccaaacttga gagactggac agtaagacag atcctgccag taacacaaaa    2820
ttaatagcaa tgaaaactga aaggaggag atgagctttg agcctggtga ccagcctggc    2880
agtgagctgg acaacttgga ggagattttg atgatttgc agaatagtca attaccacag     2940
cttttcccag acacgaggcc aggcgcccct gctggatcag ttgacaagca agccatcatc    3000
aatgacctca tgcaactcac agctgaaaac agccctgtca cacctgttgg agcccagaaa    3060
```

```
acagcactgc gaatttcaca gagcactgat tataaagatg atgatgataa ataaggatcc    3120
ttaccttaca gatctgcatc gcaggatgct gctggctacc ctgtggaaca cctacatctg    3180
tattaacgaa gcgctaaccg tttttatcag gctctgggag gcagaataaa tgatcatatc    3240
gtcaattatt acctccacgg ggagagcctg agcaaactgg cctcaggcat ttgagaagca    3300
cacggtcaca ctgcttccgg tagtcaataa accggtaaac cagcaataga cataagcggc    3360
tatttaacga ccctgccctg aaccgacgac cgggtcgaat ttgctttcga atttctgcca    3420
ttcatccgct tattatcact tattcaggcg tagcaccagg cgtttaaggg caccaataac    3480
tgccttaaaa aaattacgcc ccgccctgcc actcatcgca gtactgttgt aattcattaa    3540
gcattctgcc gacatggaag ccatcacaga cggcatgatg aacctgaatc gccagcggca    3600
tcagcacctt gtcgccttgc gtataatatt tgcccatggt gaaaacgggg gcgaagaagt    3660
tgtccatatt ggccacgttt aaatcaaaac tggtgaaact cacccaggga ttggctgaga    3720
cgaaaaacat attctcaata aaccctttag ggaaataggc caggttttca ccgtaacacg    3780
ccacatcttg cgaatatatg tgtagaaact gccggaaatc gtcgtggtat tcactccaga    3840
gcgatgaaaa cgtttcagtt tgctcatgga aaacggtgta acaagggtga acactatccc    3900
atatcaccag ctcaccgtct ttcattgcca tacg                                3934
```